(12) United States Patent
Jung

(10) Patent No.: US 11,286,097 B2
(45) Date of Patent: Mar. 29, 2022

(54) PROTECTIVE PACKAGING STRUCTURE FOR COMPRESSIBLE MATERIALS

(71) Applicant: ETS Technology Holdings LLC, Rolla, MO (US)

(72) Inventor: Steven B. Jung, Rolla, MO (US)

(73) Assignee: ETS Technology Holdings LLC, Rolla, MO (US)

( * ) Notice: Subject to any disclaimer, the term of this patent is extended or adjusted under 35 U.S.C. 154(b) by 26 days.

(21) Appl. No.: 15/890,788

(22) Filed: Feb. 7, 2018

(65) Prior Publication Data

US 2018/0222656 A1    Aug. 9, 2018

Related U.S. Application Data

(60) Provisional application No. 62/456,180, filed on Feb. 8, 2017.

(51) Int. Cl.
*B65D 77/04*       (2006.01)
*B65D 81/107*      (2006.01)
(Continued)

(52) U.S. Cl.
CPC ........ *B65D 77/0406* (2013.01); *A61F 2/0095* (2013.01); *A61F 13/00072* (2013.01);
(Continued)

(58) Field of Classification Search
CPC ............ B65D 77/0406; B65D 81/1075; B65D 85/07; B65D 81/133; B65D 81/113; B65D 81/03; B65D 5/503; B65D 25/10; B65D 75/22; A61F 13/00072; A61F 13/00076; A61F 2/0095; A61L 27/10
(Continued)

(56) References Cited

U.S. PATENT DOCUMENTS

| | | | | | |
|---|---|---|---|---|---|
| 4,557,379 | A | * | 12/1985 | Lane ...................... | B65D 75/22 206/709 |
| 5,423,477 | A | * | 6/1995 | Valdman .............. | B65D 81/264 229/104 |
| 5,706,951 | A | * | 1/1998 | Oinuma ............ | H01L 21/67366 206/592 |
| 5,954,203 | A | * | 9/1999 | Marconi .............. | B65D 43/162 206/464 |

(Continued)

FOREIGN PATENT DOCUMENTS

| | | |
|---|---|---|
| CN | 105819074 A | 8/2016 |
| CN | 205819858 U | 12/2016 |
| EP | 0076895 A2 | 4/1983 |

OTHER PUBLICATIONS

International Search Report and Written Opinion for PCT/US2018/017250 dated Apr. 25, 2018.

(Continued)

*Primary Examiner* — Rafael A Ortiz
(74) *Attorney, Agent, or Firm* — Farber LLC

(57) ABSTRACT

A more robust packaging structure for maintaining the integrity of compressible biologically active materials during storage and especially during transportation is provided. These containers protect the materials from shock, vibration, deformation, or separation from agitation. The compressible materials may be in the form of synthetic fibers, and may include a composite of fibers and beads or granules. Suitable materials that may benefit from such a robust packaging structure include synthetic materials that comprise a biologically active ceramic or glass.

23 Claims, 4 Drawing Sheets

(51) Int. Cl.
    *B65D 81/133*      (2006.01)
    *A61L 27/50*      (2006.01)
    *B65D 85/07*      (2017.01)
    *B65D 25/10*      (2006.01)
    *A61F 13/00*      (2006.01)
    *A61L 27/10*      (2006.01)
    *B65D 75/22*      (2006.01)
    *A61F 2/00*      (2006.01)
    *B65D 5/50*      (2006.01)
    *B65D 81/113*      (2006.01)

(52) U.S. Cl.
    CPC ............... *A61L 27/10* (2013.01); *A61L 27/50* (2013.01); *B65D 25/10* (2013.01); *B65D 75/22* (2013.01); *B65D 81/1075* (2013.01); *B65D 81/133* (2013.01); *B65D 85/07* (2018.01); *B65D 5/503* (2013.01); *B65D 81/113* (2013.01)

(58) Field of Classification Search
    USPC .... 206/521, 406, 433, 521.3, 594, 593, 440, 206/814, 371, 734, 551
    See application file for complete search history.

(56) References Cited

U.S. PATENT DOCUMENTS

| | | | |
|---|---|---|---|
| 6,595,366 B1* | 7/2003 | Brown | B65D 43/0222 206/525 |
| 2003/0146128 A1* | 8/2003 | Sakai | B65D 5/5021 206/583 |
| 2005/0150801 A1* | 7/2005 | Tippey | B65D 5/68 206/440 |
| 2007/0175779 A1* | 8/2007 | Imai | B65D 11/188 206/308.3 |
| 2009/0092738 A1* | 4/2009 | Shew | A47G 23/06 426/665 |
| 2013/0233736 A1 | 9/2013 | Hess et al. | |

OTHER PUBLICATIONS

International Preliminary Report on Patentability for PCT/US2018/017250 dated Aug. 22, 2019.

Office Action for corresponding Chinese Appl. No. 201880010975.9 dated Sep. 2, 2020.

Examination Report for EP Appl. No. 18706130.4 dated Aug. 7, 2020.

Office Action for corresponding Israeli Appl. No. 268539 dated Sep. 29, 2021.

* cited by examiner

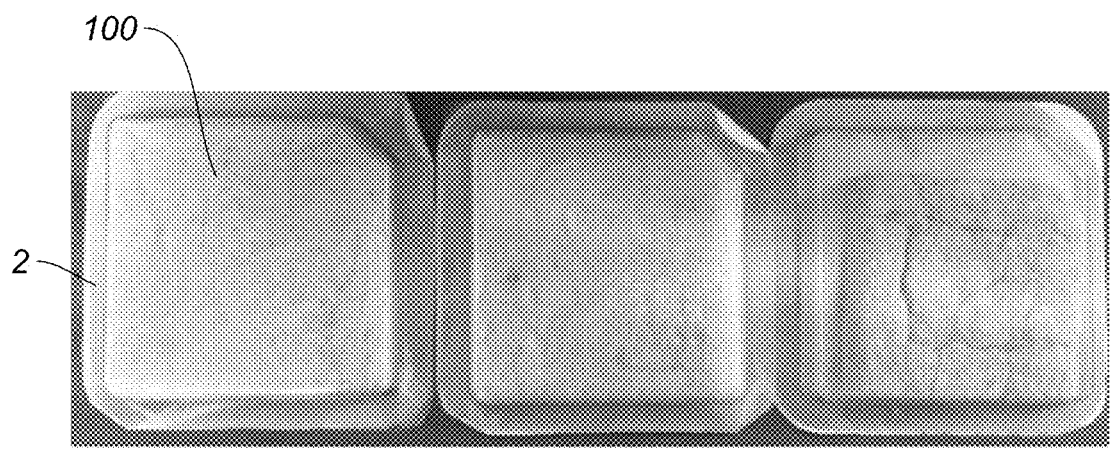
FIG. 1A
(Prior Art)
FIG. 1B
(Prior Art)
FIG. 1C
(Prior Art)
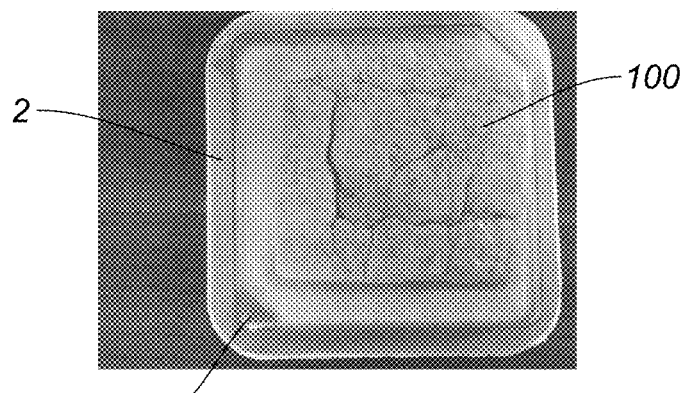
FIG. 2
(Prior Art)

PROTECTIVE PACKAGING STRUCTURE FOR COMPRESSIBLE MATERIALS

CROSS-REFERENCE TO RELATED APPLICATIONS

This application claims benefit of U.S. Provisional No. 62/456,180 filed Feb. 8, 2017 and entitled "PROTECTIVE PACKAGING STRUCTURE FOR COMPRESSIBLE MATERIALS," the contents of which are incorporated in their entirety by reference.

FIELD

The present disclosure relates to packaging structures for the storage or transportation of materials sensitive to shock, vibration, deformation, or separation from agitation. More specifically, the present disclosure relates to storage containers and packaging methods for the storage or transportation of compressible biologically active materials. Even more specifically, these storage containers and the associated packaging methods protect the compressible biologically active materials, which may include composite fibers and granules, from shock, vibration, deformation, or separation from agitation during storage and while being transported.

BACKGROUND

Over the past decade, there have been many new advancements in the field of tissue regeneration and wound care. One such advancement is in the area of materials science and the development of novel synthetic graft materials that include biologically active ceramics and glass. Today, biologically active glass products in fiber form are available for tissue scaffolding, and have shown great potential in their ability to help regrow new tissue, including both soft tissue and hard, bone tissue, as well as for wound dressings. While clinical outcomes have been favorable, the fragile and specifically compressible nature of the products themselves presents a unique challenge in terms of handling, and particularly with storage and transportation.

It is well accepted that the packaging of medical devices is just as critical as the devices themselves. Besides the very fundamental requirement to maintain the sterility of the device, superior medical technology cannot be delivered if the medical device arrives damaged. Particularly with compressible synthetic fiber materials for wound care and tissue regeneration, maintaining the integrity of these materials during transportation is critical for ensuring the product meets the advertised product specifications and the customer expectations after shipping. Glass fiber materials, especially uncoated, will compress and change shape under its own weight if stored in standard packaging arrangements such as a standard plastic tray sealed with a Tyvek or foil lid, or a plastic clamshell container. Vibrations from normal shipping activities can lead to shifting of the fibers in the package, which can lead to alterations in the shape, appearance, and function of the fibrous synthetic product. The shape change is especially critical for wound dressings in the same shelf box in that significant product variation from dressing to dressing leads to loss in customer confidence.

Accordingly, it is desirable to provide improved containers that serve to maintain the integrity of the fibrous synthetic materials during storage and especially during transportation. These containers should be able to protect the materials from shock, vibration, deformation, or separation from agitation.

SUMMARY

The present disclosure provides a more robust packaging structure for maintaining the integrity of biologically active materials during storage and especially during transportation. These containers protect the materials from shock, vibration, deformation, or separation from agitation. The materials may be in the form of synthetic fibers, and may include a composite of fibers and beads or granules. According to one aspect of the disclosure, suitable materials that may benefit from such a robust packaging structure include synthetic materials that comprise a biologically active ceramic or glass.

In one exemplary embodiment of the present disclosure, a protective packaging structure for transporting compressible materials is provided. The protective packaging structure may comprise a containment unit having a first, lower shell and a second, upper shell. The first, lower shell may include one or more wells for receiving a compressible material therein, each of the one or more wells having a surface feature to facilitate containment and reduce movement of the compressible material within the one or more wells. The second, upper shell may be configured to nest against the first, lower shell to form a closed container. The upper shell may further have one or more raised portions for defining discrete geometries of the compressible material.

According to one aspect of the disclosure, the closed container may be configured to exert a compressive force against the compressive material within, and protect the compressive material from shock, vibration, deformation, or separation from agitation, when inside the closed container.

According to another aspect of the disclosure, the compressive force may be a vacuum force or a mechanical force. The containment unit may be configured to provide a gradient of pressure across its surface, such that different pressures are exerted against the material residing within the containment unit from one region to another, and across the surface area of the material.

Further, the containment unit may include various surface features on either the upper or lower part of the containment unit to assist in maintaining the position of the material and reduce or eliminate any shifting within the containment unit, as well as to provide visual cues for the clinician to measure, cut or otherwise shape the material for clinical use.

In one embodiment, the packaging structure may comprise a containment unit having two wells. In another embodiment, the packaging structure may comprise a containment unit having four wells.

In one embodiment, the packaging structure may comprise first and second shells that are separate components and configured to snap onto one another. In another embodiment, the packaging structure may comprise first and second shells that are connected on one side to form a clamshell.

According to one aspect of the disclosure, at least one of the shells may be formed of a clear material for visualization of the compressible material therein. According to another aspect, the second, upper shell may be configured to screw onto the first, lower shell. For instance, in one example, the first and second shells may be cylindrical, circular or otherwise round, and include threads to interlock together. According to still another aspect of the disclosure, the second, upper shell may include a handle.

In one embodiment, the first, lower shell may include surface features comprising spikes, barbs, bumps, ridges, teeth, an etched surface or a roughened surface. The surface feature of the first, lower shell may reside on a bottom surface of the shell, or on a side surface of the shell.

According to one aspect of the disclosure, the first and second shells may be configured to form a re-closeable seal when attached together. According to another aspect of the disclosure, one or more raised portions on the second, upper shell may create hatch marks within which are square or rectangular geometries. The first and second shells may be configured to form a mold tray for the compressible material when attached together.

According to one aspect of the disclosure, the packaging structure may be useful for compressible materials that comprise a porous, fibrous and hydrophilic biologically active material. According to another aspect of the disclosure, the sealed container may be configured to prevent gases, liquids and debris from passing therethrough.

According to one aspect of the disclosure, the thickness of the first, lower shell or the second, upper shell may be non-uniform throughout. According to another aspect of the disclosure, the surface feature of the first, lower shell may be uniformly distributed throughout the bottom surface of the shell. According to still another aspect of the disclosure, the surface feature may create visual cutting guides for cutting the compressible material, and/or may create visual measurement guides for measuring a size of the compressible material.

In one exemplary embodiment, the surface feature of the first, lower shell may comprise uniformly sized features, while in another exemplary embodiment, the surface feature of the first, lower shell may comprise non-uniformly sized features.

According to one aspect of the disclosure, the packaging structure creates a sealed container may be configured to provide a gradient of compression force throughout. According to another aspect of the disclosure, the packaging structure may be configured to maintain the compressible material in a sterile condition when sealed.#

In another exemplary embodiment of the present disclosure, a kit for tissue repair is provided. The kit may comprise a compressible composition of biologically active glass fibers and beads, and a protective packaging structure for transporting the composition. The protective packaging structure may comprise a containment unit having a first, lower shell and a second, upper shell. The first, lower shell may include one or more wells for receiving a compressible material therein, each of the one or more wells having a surface feature to facilitate containment and reduce movement of the compressible material within the one or more wells. The second, upper shell may be configured to nest against the first, lower shell to form a closed container. The upper shell may further have one or more raised portions for defining discrete geometries of the compressible material.

According to one aspect of the kit, the closed container may be configured to exert a compressive force against the compressive material within, and protect the compressive material from shock, vibration, deformation, or separation from agitation, when inside the closed container.

According to another aspect of the kit, the compressive force may be a vacuum force or a mechanical force. The containment unit may be configured to provide a gradient of pressure across its surface, such that different pressures are exerted against the material residing within the containment unit from one region to another, and across the surface area of the material.

Further, the containment unit may include various surface features on either the upper or lower part of the containment unit to assist in maintaining the position of the material and reduce or eliminate any shifting within the containment unit, as well as to provide visual cues for the clinician to measure, cut or otherwise shape the material for clinical use.

In one embodiment, the packaging structure may comprise a containment unit having two wells. In another embodiment, the packaging structure may comprise a containment unit having four wells.

In one embodiment, the packaging structure may comprise first and second shells that are separate components and configured to snap onto one another. In another embodiment, the packaging structure may comprise first and second shells that are connected on one side to form a clamshell.

According to one aspect of the kit, at least one of the shells may be formed of a clear material for visualization of the compressible material therein. According to another aspect, the second, upper shell may be configured to screw onto the first, lower shell. For instance, in one example, the first and second shells may be cylindrical, circular or otherwise round, and include threads to interlock together. According to still another aspect of the disclosure, the second, upper shell may include a handle.

In one embodiment, the first, lower shell may include surface features comprising spikes, barbs, bumps, ridges, teeth, an etched surface or a roughened surface. The surface feature of the first, lower shell may reside on a bottom surface of the shell, or on a side surface of the shell.

According to one aspect of the kit, the first and second shells may be configured to form a re-closeable seal when attached together. According to another aspect of the kit, one or more raised portions on the second, upper shell may create hatch marks within which are square or rectangular geometries. The first and second shells may be configured to form a mold tray for the compressible material when attached together.

According to one aspect of the kit, the protective packaging structure may be useful for compressible materials that comprise a porous, fibrous and hydrophilic biologically active material. According to another aspect of the kit, the sealed container may be configured to prevent gases, liquids and debris from passing therethrough.

According to one aspect of the kit, the thickness of the first, lower shell or the second, upper shell may be non-uniform throughout. According to another aspect of the kit, the surface feature of the first, lower shell may be uniformly distributed throughout the bottom surface of the shell. According to still another aspect of the kit, the surface feature may create visual cutting guides for cutting the compressible material, and/or may create visual measurement guides for measuring a size of the compressible material.

In one exemplary embodiment, the surface feature of the first, lower shell may comprise uniformly sized features, while in another exemplary embodiment, the surface feature of the first, lower shell may comprise non-uniformly sized features.

According to one aspect of the kit, the protective packaging structure may create a sealed container configured to provide a gradient of compression force throughout. According to another aspect of the kit, the protective packaging structure may be configured to maintain the compressible material in a sterile condition when sealed.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 1A, 1B and 1C are photographs of prior art packaging structures containing glass fiber wound care dressings after shipment.

FIG. 2 is another photograph of a prior art packaging structure containing a glass fiber wound care dressing after shipment.

FIGS. 4A and 4B illustrate another exemplary embodiment of a packaging structure of the present disclosure, in which FIG. 4A shows a top-down view of a lower shell, while FIG. 4B illustrates a top-down view of an upper lid for use with the lower shell of FIG. 4A.

FIGS. 5A and 5B are photographs of the packaging structure of FIGS. 4A and 4B containing a glass fiber wound care dressing, in which FIG. 5A shows a photograph of the packaging structure and glass fiber wound care dressing in a closed state, while FIG. 5B shows a photograph of the glass fiber wound care dressing removed from the packaging structure of FIG. 5A.

DESCRIPTION OF THE EMBODIMENTS

Figure 3:
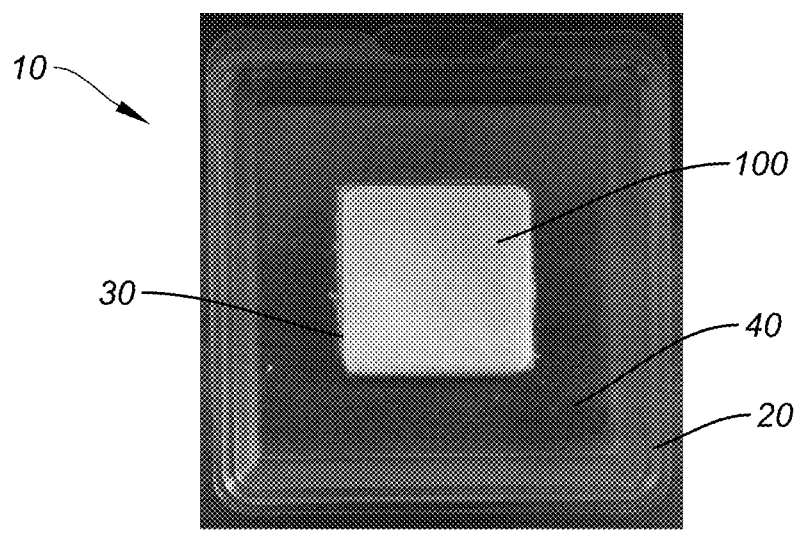
FIG. 3 is a photograph of an exemplary embodiment of a packaging structure of the present disclosure containing a glass fiber wound care dressing.

The present disclosure provides a more robust packaging structure for maintaining the integrity of biologically active materials during storage and especially during transportation. These containers protect the materials from shock, vibration, deformation, or separation from agitation. The materials may be in the form of synthetic fibers, and may include a composite of fibers and beads or granules. In some embodiments, the materials may comprise a biologically active ceramic or glass. For example, fibrous composite materials of the type described in U.S. Pat. Nos. 8,173,154, 8,535,710, and 8,821,919 may benefit from the use of the various packaging structures of the present disclosure.

The improvements in fiber packaging provided in this disclosure allow for more rigorous handling prior to use. Since the vibration of normal shipping and handling have now been addressed with the improved fiber packaging, new applications of the material are now possible. The fiber material may now be utilized by individuals such as first responders or military personal located in-theater or at forward military positions. The new compression packaging can give the fibers the capability of handling shocks and vibration on a regular basis while being carried in a soldier's backpack or riding on rough terrain in a vehicle.

Immobilization of synthetic fibers, particularly compressible synthetic fiber materials comprising bioactive glass or ceramic for wound care dressing and tissue regeneration, is critical for ensuring the product meets the advertised product specifications and the customer expectations after shipping. Glass fiber materials, especially uncoated, will compress and change shape under its own weight if stored in standard packaging arrangements such as a standard plastic tray sealed with a Tyvek or foil lid, or a plastic clamshell container. Vibrations from normal shipping activities can lead to shifting of the fiber in the package, which can lead to alterations in the shape, appearance, and function of the wound care product. The shape change is especially critical for dressings in the same shelf box, in that significant product variation from dressing to dressing leads to loss in customer confidence.

Turning now to the illustrations, FIGS. 1A, 1B and 1C represent photographs of three individual glass fiber dressings 100 stored in single-unit containers 2 of the prior art that were pulled from a single shelf box after standard shipping. Meaning, each of the single-unit containers 2 were shipped together in the same box. As clearly shown in the photographs, the range in appearance and size of the contents varies from one container 2 to the next, even though these containers 2 were shipped at the same time and in the same box. The left unit (FIG. 1A) shows approximately 100% fill, while the middle unit (FIG. 1B) shows approximately 90% fill, and the right unit (FIG. 1C) shows approximately 75% fill. In addition, there are noticeable creases and folds forming in the dressing 100 of FIG. 1C on the right. Further, there is evidence of the fiber material separating or breaking down, as visible in the same dressing 100 of FIG. 1C. Thus, it is clear that each of the three dressings 100 contained within the single-unit containers 2 of FIGS. 1A, 1B and 1C are of noticeably different size and have varying levels of folds or creases, despite having the same content (including content size and volume) at shipment, and were shipped together at the same time.

As FIG. 2 further illustrates, the presence of free flowing beads 102 that have separated from the dressing 100 and amassed in the bottom left corner of the prior art container 2 represents another significant problem with the prior art packaging today. There is minimal compression provided by the Tyvek lid closing the holding tray of the prior art container 2, and even a plastic clamshell-type design offers minimal compression after the initial closure. When the container undergoes agitation or shock during transportation, the jostling action can cause the fiber materials, some of which are composites of fibers and beads of bioactive glass, to separate much in the way a centrifuge would cause separation of a mixture of different components of different densities.

To overcome these problems with currently existing packaging, the present disclosure provides a more robust packaging structure 10 for maintaining the integrity of compressible, biologically active materials 100 during storage and especially during transportation. These containers 10 protect the materials 100 from shock, vibration, deformation, or separation from agitation. According to one aspect of the disclosure, one solution is to hold the dressing in a constant state of compression to ensure that the dressing does not change shape or lose function during shipping.

In one exemplary embodiment illustrated in FIG. 3, the packaging structure 10 may comprise a first, lower shell or tray 20 and a second, upper shell or lid 40. #The first, lower shell 20 may be defined by a bottom surface 22 surrounded by sidewalls 24, and include one or more wells 30 for receiving a compressible material 100 such as a fibrous bioactive glass material for wound care dressing or tissue regeneration. The second, upper shell 40 may be defined by a top surface 42 surrounded by sidewalls 44 and be configured to nest against the first, lower shell 20 to form a closed container. According to one aspect of the disclosure, the closed container may be configured to exert a compressive force against the compressive material within, and protect the compressive material 100 from shock, vibration, deformation, or separation from agitation, when inside the closed container 10. The compressive force may be a vacuum force or a mechanical force, as will be described in detail below.

The packaging structure 10 illustrated in FIG. 3 comprises a two piece shell design that snaps together, putting the fiber dressing 100 into a state of compression. Compression may be achieved by forming a pad of fiber with a bulk density of ~5 g/in³. As shown, the two pieces of the packaging structure 10 may be separate components that are configured to snap together or interlock. Of course, it is understood that the two pieces may also share a common side, or connect at one edge, in order to form a clamshell-type containment unit. It is also contemplated that the shells 20, 40 may include threads 32, and be configured to screw together, the upper shell being able to screw onto the bottom shell in an interlocking connection, for example, as shown in the exemplary embodiment in FIG. 6. The shells 20, 40 themselves may be round in shape. If so desired, the upper shell 40 may also include a lip or handle 46 for ease of handling (see FIG. 6). Likewise, the lower shell 20 may have a lip, flange or other gripping portion 26 for convenient handling. In some embodiments, the packaging structure 10 may be re-sealable, and the first and second shells 20, 40 can form a re-closeable seal when attached together. In other embodiments, the packaging structure 10 may be configured to maintain sterility of its contents until the seal is broken, and would therefore not be resealable.

As shown in the exemplary embodiment of FIG. 3, the lower tray 20 may comprise one single well 30 for a single unit dressing or pad 100. However, it is understood that the tray 20 may comprise more than one well 30, and for example, may comprise two or four wells, as will be shown in other examples herein. In one embodiment, the well 30 may measure approximately 2 inches×2 inches and form a square shape. However, other shapes and sizes are also contemplated for the well, such as for example, a rectangle or circle.

Moreover, one or more of the shells 20, 40 may be formed of a clear or transparent material so that the contents are clearly visible. The packaging structure 10 shown in FIG. 3 comprises a lower and upper shells (or tray and lid) 20, 40, both of which are formed of a clear material for visualization of the compressible material 100 within. Each of the shells 20, 40 may be formed of a plastic material and configured to prevent gases, liquids and debris from getting into the well 30 and contaminating or damaging the materials 100, which may be porous and/or hydrophilic and therefore susceptible to moisture or humidity.

The packaging structure of FIG. 3 provides a compressive force against the material 100 in the range of about 5 g/in³, for example. This compressive force is created when the upper and lower shells 20, 40 come together and create a mechanical force or pressure that is exerted against the compressible material 100 contained within. Alternatively, or in addition, a vacuum force may also be utilized to create the compressive force. Accordingly, the containment unit or packaging structure can be considered to act like a mold tray.

In the exemplary embodiment of FIG. 3, both shells 20, 40 of the packaging structure 10 are smooth. In other embodiments, however, one or more of the shells 20, 40 may not be smooth. In addition to the immobilization of the fibrous material 100 that comes from the shells 20, 40 once pressed together, dimensional features molded into the plastic shells 20, 40 may enhance the immobilization by adding additional compression to the dressing or materials 100. In some embodiments, each of the wells 30 of the shells 20 may have a surface feature to facilitate containment and reduce movement of the compressible material 100 within the wells. For instance, patterns molded in the top and bottom of the shells 20 40 act as teeth to impart a gripping characteristic to the otherwise smooth plastic surface.

Figure 4A:
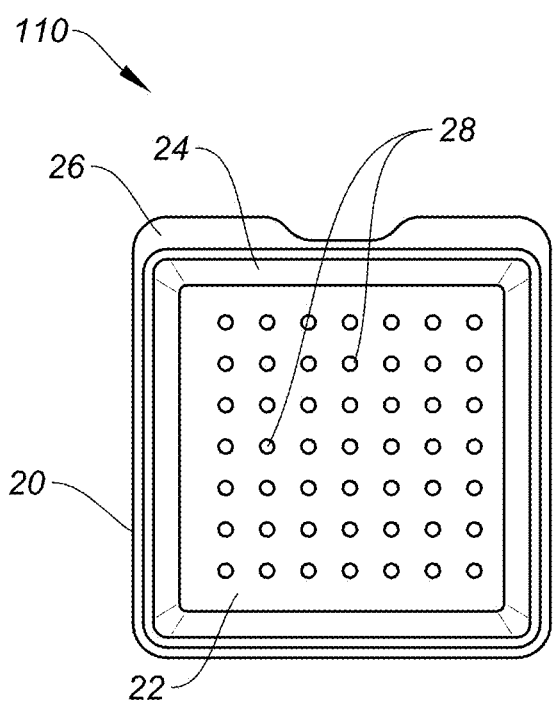
Figure 4B:
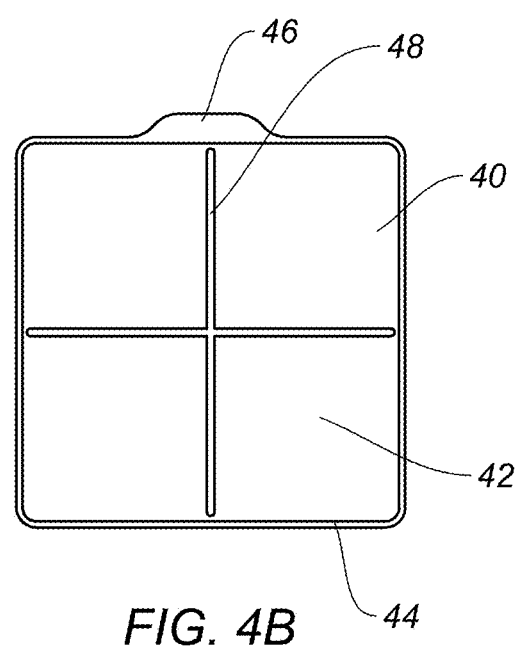

As an example, FIGS. 4A and 4B illustrate another exemplary embodiment of a packaging structure 110. Packaging structure 110 shares the same features of packaging structure 10, with like reference numerals representing the same features. FIG. 4B shows a raised surface forming a cross pattern 48 in the top surface 42 of upper shell or lid 40, while FIG. 4A shows a raised surface forming a dimpled array 28 in the bottom surface 22 of lower shell or tray 20. The added compression features 28, 48 in the shells 20, 40 reduce the movement of the dressing 100 during shipment with no noticeable change in dimensions or loss of beads 102 from the fiber matrix material 100. Another embodiment may have a raised surface pattern covering some or the entire top and/or bottom surface of each shell 20, 40, in order to add surface attachment enhancement or grip across the entire fiber dressing 100, rather than a flat surface. It is envisioned that any feature that imparts a force in a localized area may be incorporated into the embodiments described herein. For instance, another embodiment may use both the patterns and the textured surface.

Suitable compression or surface features can include, for example, spikes, barbs, bumps, ridges, teeth, etchings or surface roughenings. These surface features can be found on the bottom of the first, lower shell 20. However, the surface features may also be provided on the side surfaces 24 or of the well 30, as well as on the second, upper shell 40. The compression features of the packaging structure 10 of FIGS. 4A and 4B are uniformly distributed across the bottom of the lower shell 20. In the example shown, the dimples 28 are uniformly spaced apart about 0.5 inches from one another. However, it is contemplated that in other embodiments the compression features may be arranged in a non-uniform array or pattern, in order to provide a gradient of compressive forces across the packaging structure 10. For instance, the compression features may be arranged in a starburst pattern, with a greater concentration of the features in the center, as the features radiate outwards to the edges. In another embodiment, the compression features may be all uniformly sized. In still another embodiment, the compression features may be differently sized relative to one another, to create a non-uniform compression force within the packaging structure 20. Still in other embodiments, the type or shape or style of compression features may be non-uniform such that a combination of different features can be utilized on the same shell, such as for example, a combination of dimples and etchings either uniformly or non-uniformly arranged across the shells 20, 40.

Figure 5A:
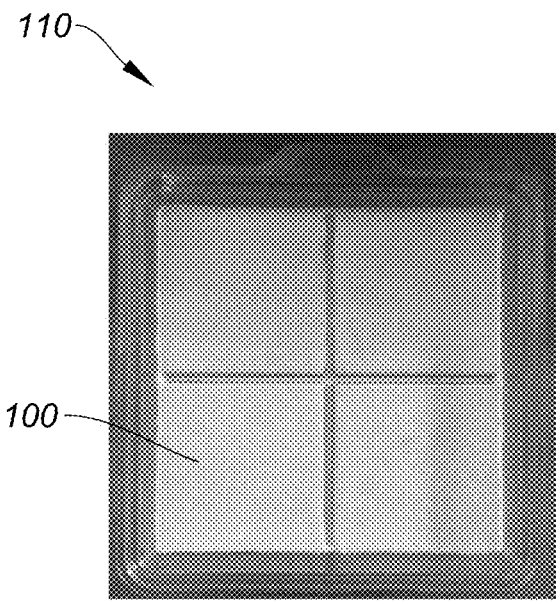
Figure 5B:
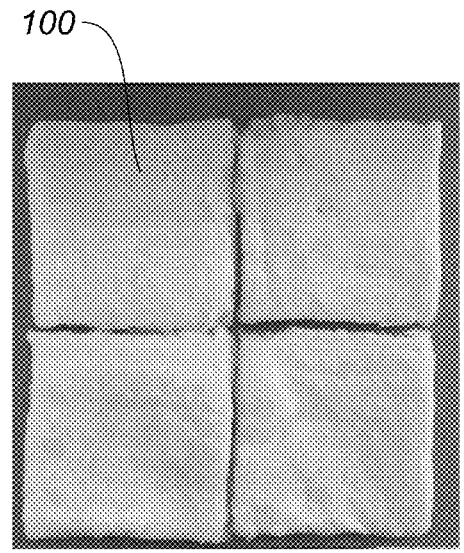

In another aspect of the disclosure, certain features of the fiber immobilization system can additionally aid the clinician in application of the dressing. As an example, as shown in FIG. 4B, the upper shell or lid 40 may have one or more raised portions 48 for defining discrete geometries of the compressible material. For instance, these raised portions create hatch marks 48 such that, when used with the compressible material as shown in FIG. 5A, the cross pattern of raised portions 48 built into the top piece of the packaging structure 10 actually can impart some indentations into the dressing 100 that make separating the material 100 into four (4) 2×2 dressings or squares of material simpler, and eliminates the need for scissors. These hatch marks 48 can define discrete geometries such as a square or rectangular shape, and as shown, can provide indentation marks on the material 100 that serves to score the material for ease of separation. FIG. 5B shows how the material is easily separated into these discrete geometries without requiring cutting tools. In this way, the packaging structure 10 of the present disclosure also serves as a molding tray, allowing the materials 100 to be maintained in a defined shape during storage and transportation until its use.

As shown, the hatch marks 48 can create distinct squares of materials for use as dressing or tissue scaffolds. However, other configurations of indentations could be used, but the concept is the same for adding functionality by immobilizing the dressing until use, and allowing the clinician to more easily conform the dressing to the needs of the patient. Additionally, the dimples 28 formed at the bottom of the dressing would allow the clinician to have a visual measurement tool as well as a cutting guide for cutting shapes that are not defined by the top cross hatch 48. For example, for a wound that was 2.5" in length, a dimple array of 0.5 inches would allow the clinician to simply count out 5 of the dimples and cut, as opposed to trying to measure and somehow mark the dressing before cutting. These additions save time for the clinician and increase value, especially in surgery where time is critical.

Figure 6:
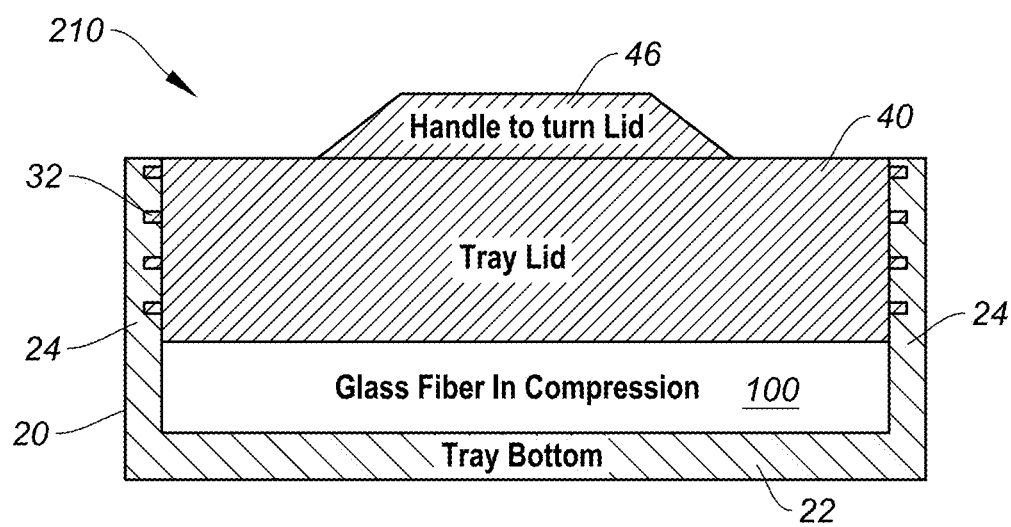
FIG. 6 is a cross-sectional view of still another exemplary embodiment of a packaging structure of the present disclosure containing a glass fiber material.

The packaging structures of the present disclosure may be configured to provide compression of the fiber material to an average volumetric density in the range of: about 0.5 g/in$^3$ to 20 g/in$^3$, or about 1 g/in$^3$ to 10 g/in$^3$, or even about 2 g/in$^3$ to 5 g/in$^3$. As represented in FIG. 6, in another exemplary embodiment the packaging structure 210 may provide uniform compression force against the fiber material 100 contained within it. This can be accomplished with a packaging structure 210 employing threads 32 to allow the upper shell 40 to secure onto the lower shell 20, and exert an even, uniform force onto the contained material 100 once the two shells 20, 40 are locked together.

However, in another aspect of the present disclosure, the packaging structures may be configured to provide a gradient of compression pressures against the fiber material 100. This can be accomplished, for example, by using a gradient of fiber density for fixation, or using multiple modes (i.e., two or more) of compression with different density profiles to mechanically fix the fiber material 100. Examples of multiple modes of compression density can be achieved using a combination of features such as the flat surface, cross hatch 48, or dimpled surface 28 to affect the fiber density.

Figure 7:
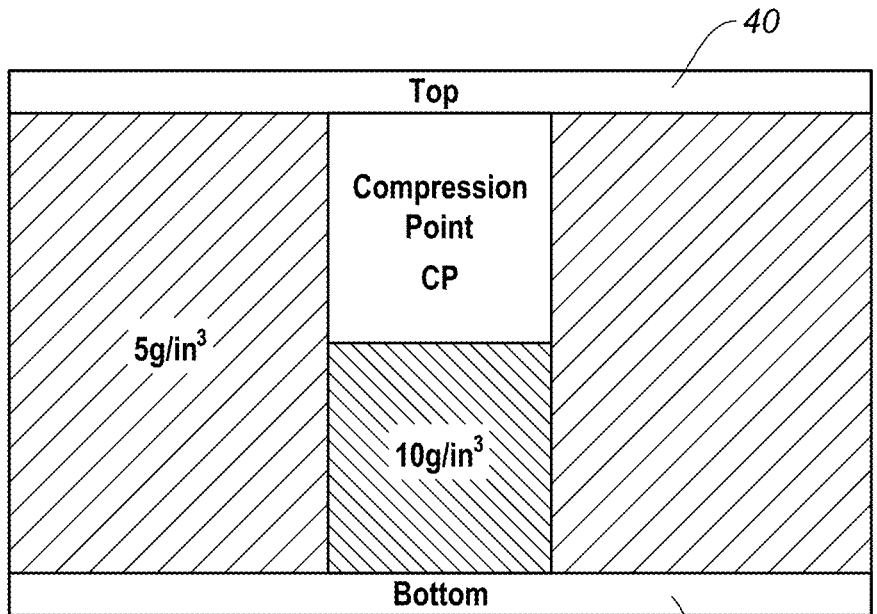
FIG. 7 is a cross-sectional view of yet another exemplary embodiment of a packaging structure of the present disclosure having a gradient of compression forces.
Figure 8:
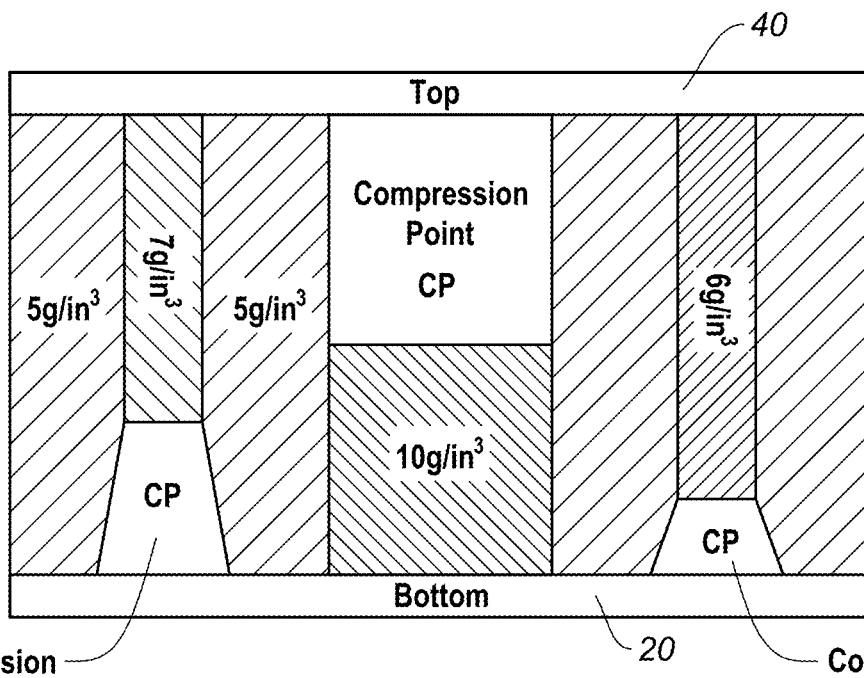
FIG. 8 is a cross-sectional view of even still another exemplary embodiment of a packaging structure of the present disclosure having a gradient of compression forces.

FIGS. 7 and 8 illustrate exemplary embodiments of packaging structures that provide a gradient of compression forces on the material contained within it. As shown, various fiber densities due to compression can be achieved by providing a higher average density in one region compared to another region of the same packaging structure by adjusting the amount of compression at that region. One way to achieve the different compression force is to vary the thickness of the shell, either one or both 20, 40. For example, as FIG. 7 illustrates, a raised portion in the center of the upper shell 40 would create a greater compression force or compression point, CP, in that region when the two shells 20, 40 are attached. As FIG. 8 illustrates, additional smaller raised portions may be provided on the lower shell 20 which, when used with the upper shell 40 of FIG. 7, would create a gradient of compression pressures (all due to mechanical force exerted against the fiber material) across the surface of the packaging structure. As shown, compression points CP vary and can range from 6 g/in$^3$ to 10 g/in$^3$ at varying regions of the packaging structure.

Kits for tissue repair can be provided which would include the packaging structure disclosed herein along with a compressible fibrous material suitable for tissue repair and wound care dressing, such as a composition of biologically active glass fibers and beads. The packaging structure comprises a closed container that could prevent the separation of the fibers and beads from shock or vibration, such as during transportation, and help to maintain the materials in a sterile condition.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A protective packaging structure for transporting a compressible bioactive material, the structure comprising:
   a containment unit having first and second shells,
   the first shell including one or more wells for receiving the compressible bioactive material therein, and a surface feature to facilitate containment and reduce movement of the compressible bioactive material within the one or more wells,
   the second shell being configured to nest against the first shell to form a closed container configured to provide compression pressure against the compressible bioactive material, and comprising a substantially linear raised portion extending substantially from a first surface to an opposite second surface of the closed container, the substantially linear raised portion being a first substantially linear raised portion configured to score the compressible bioactive material in the first shell for ease of separating the material into discrete geometric portions.

2. The packaging structure of claim 1, further comprising a second substantially linear raised portion extending substantially from a third surface to a fourth opposite surface of the closed container.

3. The packaging structure of claim 2, wherein the first and second substantially linear raised portions intersect each other to form four wells within the closed container.

4. The packaging structure of claim 3, wherein the first and second substantially linear raised portions are configured to score the compressible bioactive material into four separate portions.

5. The packaging structure of claim 1, wherein one of the first and second shells has a substantially flat interior surface.

6. The packaging structure of claim 1, wherein one of the first and second shells comprises a lid configured to form a recloseable seal with the other shell.

7. The packaging structure of claim 1, wherein the first and second shells each have an inner surface, wherein the substantially linear raised portion extends from the inner surface of the second shell substantially to the inner surface of the first shell.

8. The packaging structure of claim 1, wherein the first and second shells are configured as a mold tray for the compressible bioactive material.

9. The packaging structure of claim 1, wherein the compressible bioactive material comprises bioactive glass.

10. The packaging structure of claim 1, wherein the closed container exerts a compressive force upon the compressible bioactive material in an average volumetric density range of about 0.5 $g/in^3$ to about 20 $g/in^3$.

11. The packaging structure of claim 1, wherein the surface feature comprises an array of raised dimples extending from an inner surface of the first shell.

12. A protective packaging structure for transporting a compressible bioactive material, the structure comprising:
a containment unit having first and second shells,
the first shell including one or more wells for receiving the compressible bioactive material therein, and
the second shell being configured to nest against the first shell to form a closed container configured to provide compression pressure against the compressible bioactive material, and
wherein at least one of the first and second shells includes first and second substantially linear raised portions extending substantially from one surface to an opposite surface of the closed container, the first and second substantially linear raised portions being configured to score the compressible bioactive material in the first shell for ease of separating the material into discrete geometric portions.

13. The packaging structure of claim 12, wherein at least one of the first and second shells comprises a surface feature to facilitate containment and reduce movement of the compressible bioactive material within the one or more wells.

14. The packaging structure of claim 12, wherein the first substantially linear raised portion extends from a first to a second opposite surface of the closed container.

15. The packaging structure of claim 14, wherein the second substantially linear raised portion extends from a third to a fourth opposite surface of the closed container.

16. The packaging structure of claim 15, wherein the first and second substantially linear raised portions intersect each other to form four wells within the closed container.

17. The packaging structure of claim 12, wherein one of the two shells has a substantially flat interior surface.

18. The packaging structure of claim 12, wherein one of the first and second shells comprises a lid configured to form a recloseable seal with the other shell.

19. The packaging structure of claim 12, wherein the first and second substantially linear raised portions extend from the inner surface of the second shell substantially to the inner surface of the first shell.

20. The packaging structure of claim 12, wherein the first and second substantially linear raised portions are configured to score the compressible bioactive material into four separate portions.

21. The packaging structure of claim 12, wherein the compressible bioactive material comprises bioactive glass.

22. The packaging structure of claim 18, wherein the closed container exerts a compressive force upon the compressible bioactive material in the average volumetric density range of about 0.5 $g/in^3$ to about 20 $g/in^3$.

23. The packaging structure of claim 13, wherein the surface feature comprises an array of raised dimples extending from an inner surface of the first shell.

* * * * *